United States Patent [19]
Forman

[11] Patent Number: 5,772,632
[45] Date of Patent: *Jun. 30, 1998

[54] DILATION-DRUG DELIVERY CATHETER

[75] Inventor: Michael R. Forman, St. Paul, Minn.

[73] Assignee: Schneider (USA) Inc., Plymouth, Minn.

[*] Notice: The term of this patent shall not extend beyond the expiration date of Pat. No. 5,415,636.

[21] Appl. No.: 905,873

[22] Filed: Aug. 4, 1997

Related U.S. Application Data

[60] Continuation of Ser. No. 433,100, May 3, 1995, abandoned, which is a division of Ser. No. 227,254, Apr. 13, 1994, Pat. No. 5,415,636.

[51] Int. Cl.$^6$ .................................................. A61M 29/00
[52] U.S. Cl. .......................................... 604/101; 604/102
[58] Field of Search ............................. 604/96, 101, 102, 604/264, 265, 280; 606/192, 194

[56] References Cited

U.S. PATENT DOCUMENTS

| | | |
|---|---|---|
| 3,948,254 | 4/1976 | Zaffaroni . |
| 4,198,981 | 4/1980 | Sinnreich ................................ 128/344 |
| 4,299,226 | 11/1981 | Banka . |
| 4,417,576 | 11/1983 | Baran . |
| 4,423,725 | 1/1984 | Baran et al. . |
| 4,445,892 | 5/1984 | Hussein et al. . |
| 4,464,176 | 8/1984 | Wijayarathna . |
| 4,531,936 | 7/1985 | Gordon . |
| 4,573,966 | 3/1986 | Weikl et al. . |
| 4,610,662 | 9/1986 | Weikl et al. . |
| 4,636,195 | 1/1987 | Wolinsky . |
| 4,655,746 | 4/1987 | Daniels et al. . |
| 4,705,709 | 11/1987 | Vailanwurt ................................ 428/36 |
| 4,708,718 | 11/1987 | Daniels . |
| 4,799,479 | 1/1989 | Spears . |
| 4,824,436 | 4/1989 | Wolinsky . |
| 4,832,688 | 5/1989 | Sagae et al. . |
| 4,911,163 | 3/1990 | Fina . |
| 4,927,418 | 5/1990 | Dake et al. . |
| 4,968,306 | 11/1990 | Huss et al. . |
| 4,968,307 | 11/1990 | Dake et al. . |
| 4,983,166 | 1/1991 | Yamawaki . |
| 4,994,033 | 2/1991 | Shockey et al. . |

(List continued on next page.)

FOREIGN PATENT DOCUMENTS

| | | |
|---|---|---|
| 0383429 | 1/1990 | European Pat. Off. . |
| 0526102A1 | 7/1992 | European Pat. Off. . |
| 3915289A1 | 11/1990 | Germany . |
| 8301894 | 6/1983 | WIPO . |
| WO86/05990 | 10/1986 | WIPO . |
| WO92/11895 | 7/1992 | WIPO . |
| WO92/11896 | 7/1992 | WIPO . |

OTHER PUBLICATIONS

Stephen R. Hanson, Ph.D., "Intralumenal Drug Delivery for Experimental Thrombosis and Restenosis," *Restenosis Summit V,* May 20, 1993, pp. 296–300.

Spencer B. King III, M.D., "Localized Endovascular Therapy for Interventional Cardiology," *Restenosis Summit V,* May 20, 1993, pp. 280–281.

Robert J. Levy, M.D., "Local Delivery: Polymer Methods," *Restenosis Summit V,* May 20, 1993, pp. 316–320.

Certified English Translation of DE 3915289 A1, published Nov. 15, 1990.

Certified English Translation of WO 83/01894, published Jun. 9, 1983.

*Primary Examiner*—Corrine M. McDermott
*Attorney, Agent, or Firm*—Peter C. Richardson; Lawrence C. Akers; Philip C. Strassburger

[57] ABSTRACT

A dilation-drug delivery catheter comprises a dilation portion for dilating a stenosis and a drug delivery portion for delivering antithrombolytic, antiproliferative, or any other type of medication, to the dilation site. The drug delivery portion of the catheter is located within the dilation portion, which can be retracted to reveal the drug delivery portion, after dilation. Occlusion balloons are preferably provided on the drug delivery portion to isolate the dilation site during drug delivery.

4 Claims, 5 Drawing Sheets

U.S. PATENT DOCUMENTS

| | | |
|---|---|---|
| 5,019,075 | 5/1991 | Spears et al. . |
| 5,021,044 | 6/1991 | Sharkawy . |
| 5,049,132 | 9/1991 | Shaffer et al. . |
| 5,059,178 | 10/1991 | Ya ............................................. 604/101 |
| 5,087,244 | 2/1992 | Wolinsky et al. . |
| 5,090,960 | 2/1992 | Don Michael . |
| 5,092,841 | 3/1992 | Spears . |
| 5,098,381 | 3/1992 | Schneider . |
| 5,102,402 | 4/1992 | Dror et al. . |
| 5,112,305 | 5/1992 | Barath et al. . |
| 5,129,883 | 7/1992 | Black ........................................ 604/101 |
| 5,135,484 | 8/1992 | Wright . |
| 5,163,905 | 11/1992 | Don Michael . |
| 5,176,638 | 1/1993 | Don Michael . |
| 5,180,366 | 1/1993 | Woods . |
| 5,199,951 | 4/1993 | Spears . |
| 5,213,576 | 5/1993 | Abiuso et al. . |
| 5,222,941 | 6/1993 | Don Michael . |
| 5,236,413 | 8/1993 | Feiring . |
| 5,236,424 | 8/1993 | Imran . |
| 5,242,397 | 9/1993 | Barath et al. . |
| 5,267,959 | 12/1993 | Forman . |
| 5,314,409 | 5/1994 | Sarosiek et al. ......................... 604/101 |
| 5,320,604 | 6/1994 | Walker ....................................... 604/96 |

DILATION-DRUG DELIVERY CATHETER

This is a continuation of application Ser. No. 08/433,100, filed on May 3, 1995, now abandoned which is a divisional of Ser. No. 08/227,254, filed on Apr. 13, 1994, now U.S. Pat. No. 5,415,636.

FIELD OF THE INVENTION

A dilation-drug delivery catheter, and, more particularly, a dilation-drug delivery catheter comprising a drug delivery portion within a dilation portion, wherein the dilation portion can be retracted after dilation, revealing the drug delivery portion.

BACKGROUND OF THE INVENTION

Percutaneous transluminal angioplasty ("PTA") and percutaneous transluminal coronary angioplasty ("PTCA"), wherein a dilation balloon is advanced through the vascular system to a stenosis and inflated to open the blockage, is now a commonplace procedure. In about one-third of the cases, however, after the procedure can occur and restenosis that can require another dilation procedure. It is estimated that the total cost of restenosis requiring an additional dilation procedure or some other treatment, is over 2 billion dollars per year worldwide.

Various agents that may reduce restenosis can be applied to the dilation site. For example, antithrombolytic agents such as heparin may prevent clotting. Antiproliferative agents, such as dexamethasone, can prevent smooth muscle cell migration and proliferation.

Various methods have been proposed to effectively deliver such agents to the dilation site. For example, in U.S. Pat. No. 5,087,244, to Wolinsky, a catheter is disclosed having a thin walled flexible balloon with a plurality of small holes. After an angioplastic procedure, such a balloon can be advanced to the dilation site and inflated with heparin, or some other medication. The medication exits the inflated balloon, which is in contact with the arterial wall, through the holes. Such "weeping" balloons may damage the arterial wall, however. In addition, having to insert a second catheter for drug delivery after removal of the dilation catheter is cumbersome and time consuming. It can also be difficult to precisely locate the dilation site after the dilation catheter is removed.

It is, therefore, advantageous to provide a catheter which can both dilate the stenosis and immediately thereafter deliver drugs directly to the dilation site. U.S. Pat. Nos. 4,824,436 and 4,636,195, also to Wolinsky, disclose a catheter with a dilation balloon and a pair of occlusion balloons proximal and distal to the dilation balloon. A drug delivery conduit is provided between the distal occlusion balloon and the dilation balloon. After dilation of the stenosis, the dilation balloon is deflated, the occlusion balloons are inflated and a drug is delivered. Because of the presence of the dilation balloon, there is only a small region available for drug delivery. Drug delivery may, therefore, be slow and of too low volume to be effective.

SUMMARY OF THE INVENTION

The present invention provides a single catheter which can both dilate a stenosis and deliver an adequate supply of a desired drug directly to the dilation site. The dilation-drug delivery catheter of the present invention comprises a dilation portion including a dilation balloon attached to an outer catheter shaft. The outer catheter shaft comprises a dilation lumen for providing inflation fluid to the dilation balloon, and a central lumen. A drug delivery portion of the catheter is located at least in part within the central lumen. The drug delivery portion comprises an inner catheter shaft having at least one drug delivery port. The inner catheter shaft defines a drug delivery lumen, which provides any desired drug to the drug delivery port. The drug delivery port is typically located in a portion of the inner catheter shaft lying within the central lumen during dilation. The dilation portion of the catheter can be moved with respect to the drug delivery portion such that the dilation portion can be retracted from the distal end of the drug delivery portion after dilation, revealing the drug delivery port.

The drug delivery portion of the catheter of the present invention preferably further comprises a first occlusion balloon distal to the drug delivery port and an inflation lumen in fluid communication with the first occlusion balloon. A second occlusion balloon is preferably provided proximal to the drug delivery port. The occlusion balloons maintain the delivered drug in proximity with the dilation site. The same inflation lumen can be in fluid communication with the first and second balloons.

A plurality of drug delivery ports are preferably provided, as are perfusion means for allowing blood to flow through the dilation-drug delivery catheter, beyond the occlusion balloon.

In another aspect of the present invention, a dilation-drug delivery catheter comprises a dilation portion comprising a dilation balloon and a drug delivery portion having a distal end, wherein the portions can be moved with respect to each other. The catheter has a dilation position, wherein the distal end of the drug delivery portion is located at least in part within the dilation portion, and a drug delivery position, wherein the dilation portion is retracted to reveal the distal end of the drug delivery portion.

In another aspect of the present invention, a dilation-drug delivery catheter comprises a dilation balloon bonded to an outer catheter shaft. The catheter shaft has an outer wall and an inner wall defining a lumen for providing dilation fluid to the dilation balloon. The inner wall further defines a central lumen. An inner catheter shaft comprises a pair of occlusion balloons at its distal end, a lumen in fluid communication with the occlusion balloons to provide inflation fluid to the occlusion balloons, a plurality of drug delivery ports between the occlusion balloons, a lumen in fluid communication with the drug delivery ports to provide drugs to the ports, and a guide wire lumen. A portion of the inner catheter shaft lies within the central lumen, and the outer catheter shaft can be moved with respect to the inner catheter shaft to reveal the occlusion balloons and drug delivery ports. Preferably, the drug delivery ports lie within the central lumen prior to the outer catheter shaft being retracted.

DESCRIPTION OF THE INVENTION

Figure 1:
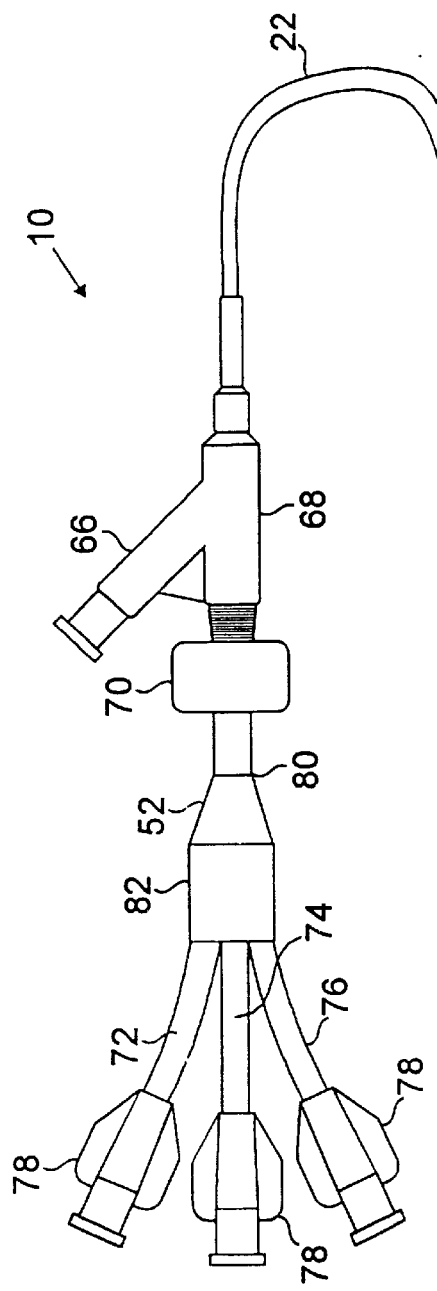
FIG. 1 is a view of a dilation-drug delivery catheter in accordance with the present invention, wherein the distal portion of the catheter is shown enlarged and in cross-section, in the dilation position of the catheter.
Figure 1:
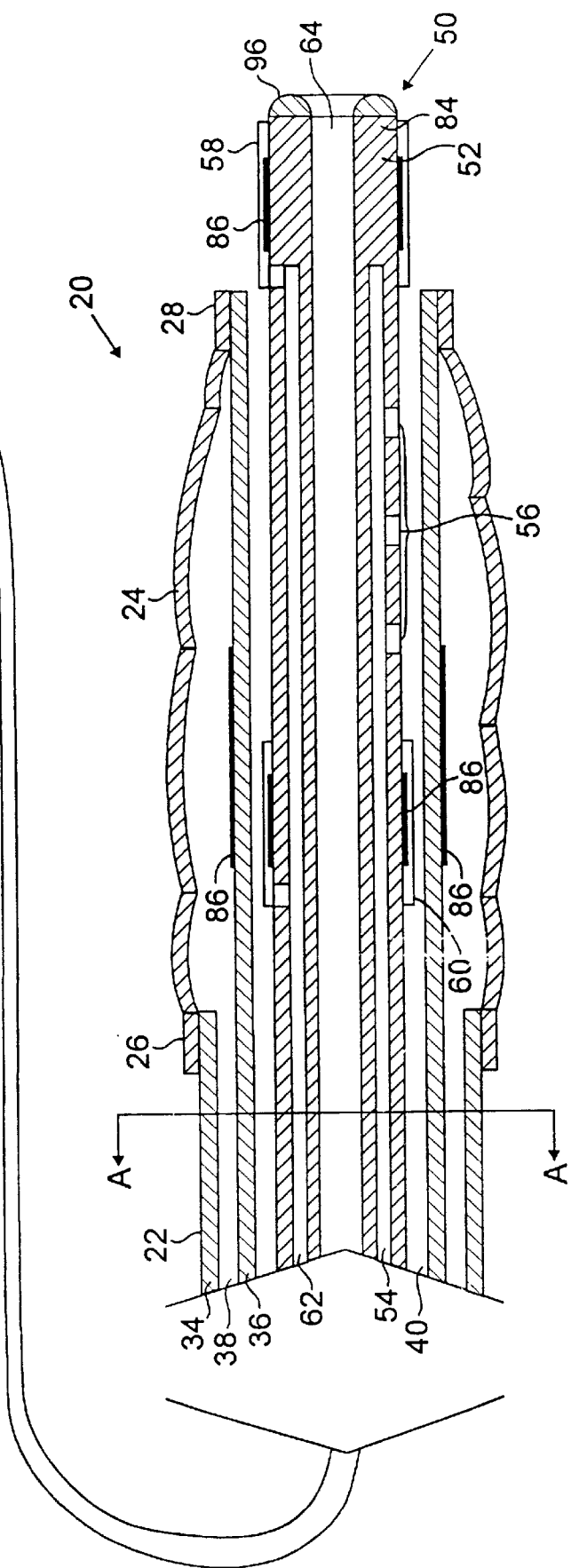
Figure 2:
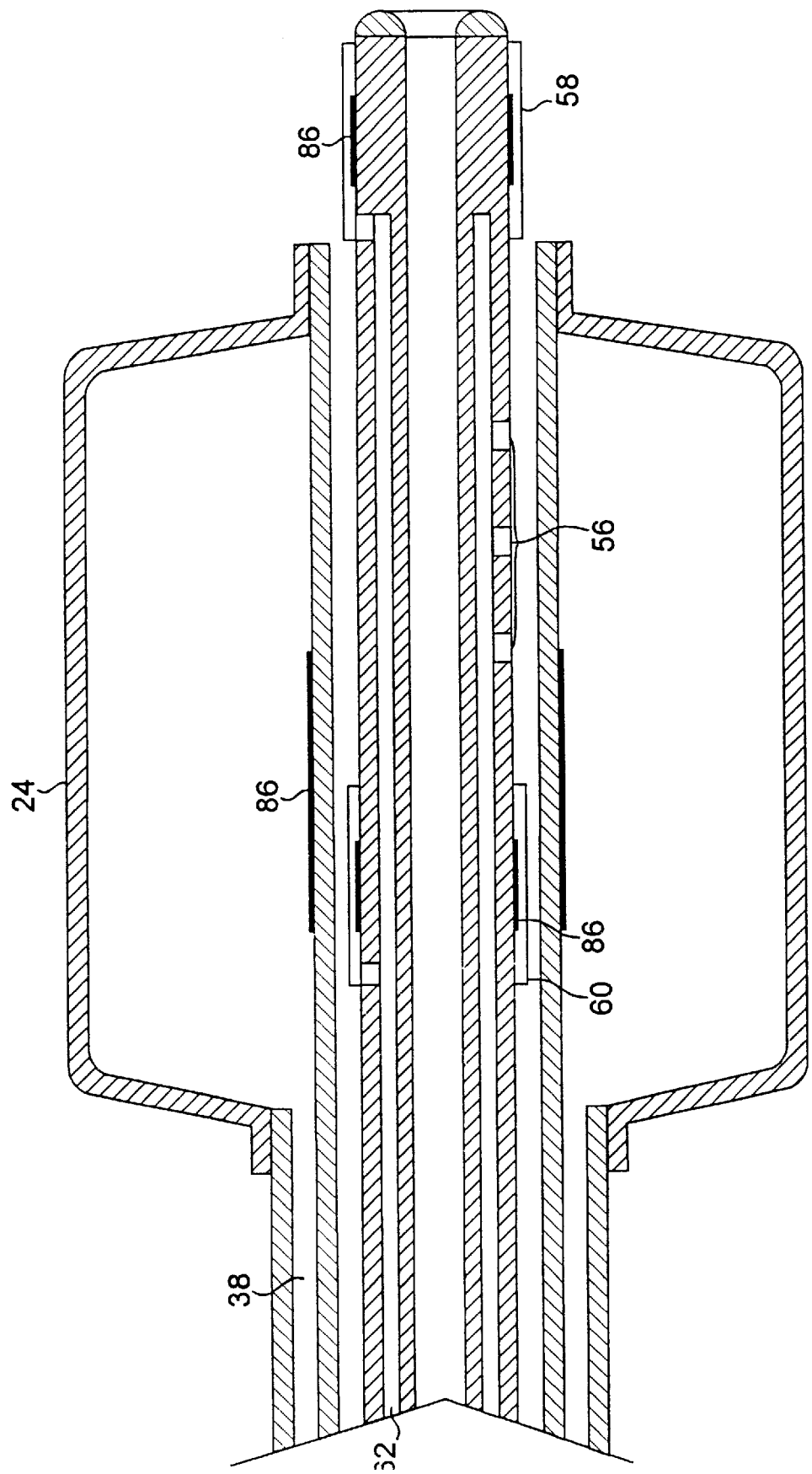
FIG. 2 is a cross-sectional view of the distal portion of the catheter of FIG. 1, wherein a dilation balloon is shown inflated.

FIG. 1 is a view of a dilation-drug delivery catheter 10 in accordance with the present invention, wherein the distal portion of the catheter 10 is shown enlarged and in cross-section. The dilation-drug delivery catheter 10 comprises a dilation portion 20 and a drug delivery portion 50. The dilation portion 20 comprises a dilation balloon 24 bonded to an outer catheter shaft 22 at sites 26 and 28. In FIGS. 1–2, the catheter 10 is shown in its dilation position. In FIG. 1, the dilation balloon 24 is deflated, while in FIG. 2, a cross-sectional view of the distal portion of the dilation-drug delivery catheter 10 of FIG. 1, the dilation balloon 24 is shown inflated.

Figure 3:
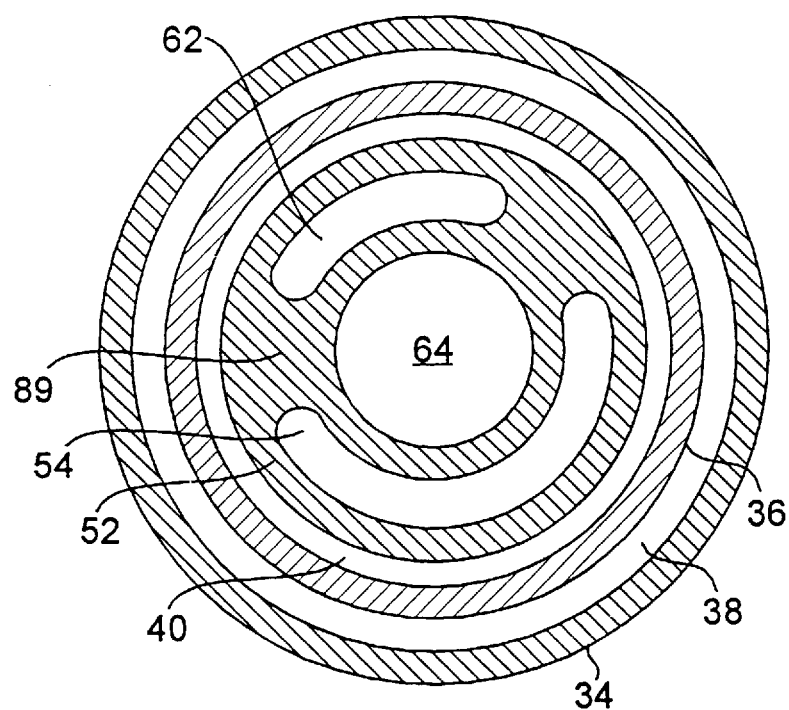
FIG. 3 is a cross-sectional view of the distal portion of the catheter of FIG. 1, along line AA of FIG. 1.

The outer catheter shaft 22 has an outer wall 34 and an inner wall 36 which define a dilation lumen 38 for providing dilation fluid to the dilation balloon 22. The inner wall 36 also defines a central lumen 40 for receiving the drug delivery portion 50. FIG. 3 is a cross-sectional view of the dilation-drug delivery catheter 10, through line A—A of FIG. 1, showing the outer wall 34, inner wall 36, the dilation lumen 38 and the central lumen 40.

The drug delivery portion 50 of the catheter 10 comprises an inner catheter shaft 52, whose distal end is located at least in part within the second lumen 40. The inner catheter shaft 52 includes a drug delivery lumen 54, which communicates with the exterior of the shaft 52 through drug delivery ports 56. There are preferably between 2–20 circular or oval shaped ports 56 with a diameter or length, respectively, of between about 0.003–0.020 inches. Three drug delivery ports 56 are provided in this embodiment. A plurality of such ports are preferably provided to ensure the delivery of adequate drug to the dilation site. The drug delivery ports 56 preferably lie within the central lumen 40 during dilation. FIG. 3 shows that the drug delivery lumen 54 is preferably semi-circular.

Returning to FIGS. 1–2, a distal occlusion balloon 58 and a proximal occlusion balloon 60 are preferably provided to isolate the dilation site during drug delivery. The occlusion balloons 58, 60 are shown inflated in the side view of FIG. 5. The occlusion balloons 58, 60 maintain the drug in proximity with the portion of the arterial wall which has been dilated, improving the absorption and efficacy of the drug. An inflation lumen 62 in the inner catheter shaft 52 is provided to convey inflation fluid to the occlusion balloons 58, 60. The inner catheter shaft 52 also typically includes a guide wire lumen 64. The inflation lumen 62 and guide wire lumen 64 are shown in cross-section in FIG. 3. The inflation lumen 62 is also preferably semi-circular and in the same radial plane as the drug delivery lumen 54. To deliver an adequate amount of drug in the time allowed, the drug delivery lumen 54 will generally need to be larger than the inflation lumen 62. In the embodiment illustrated, the portion of the inner catheter shaft 52 including the distal occlusion balloon 58 extends beyond the distal tip of the dilation portion 20 while the catheter is in its dilation position. The distal occlusion balloon 58 can lie within the second lumen 40 in the dilation position, as well.

Figure 4:
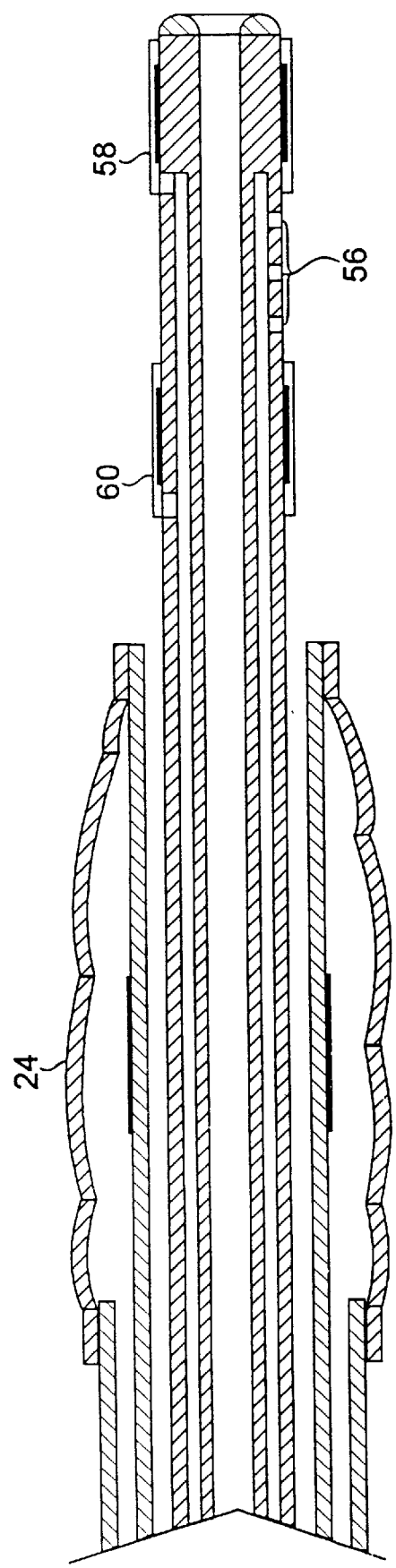
FIG. 4 is a cross-sectional view of the distal portion of the catheter of FIG. 1, with its dilation portion retracted, showing the drug delivery position of the catheter.
Figure 5:
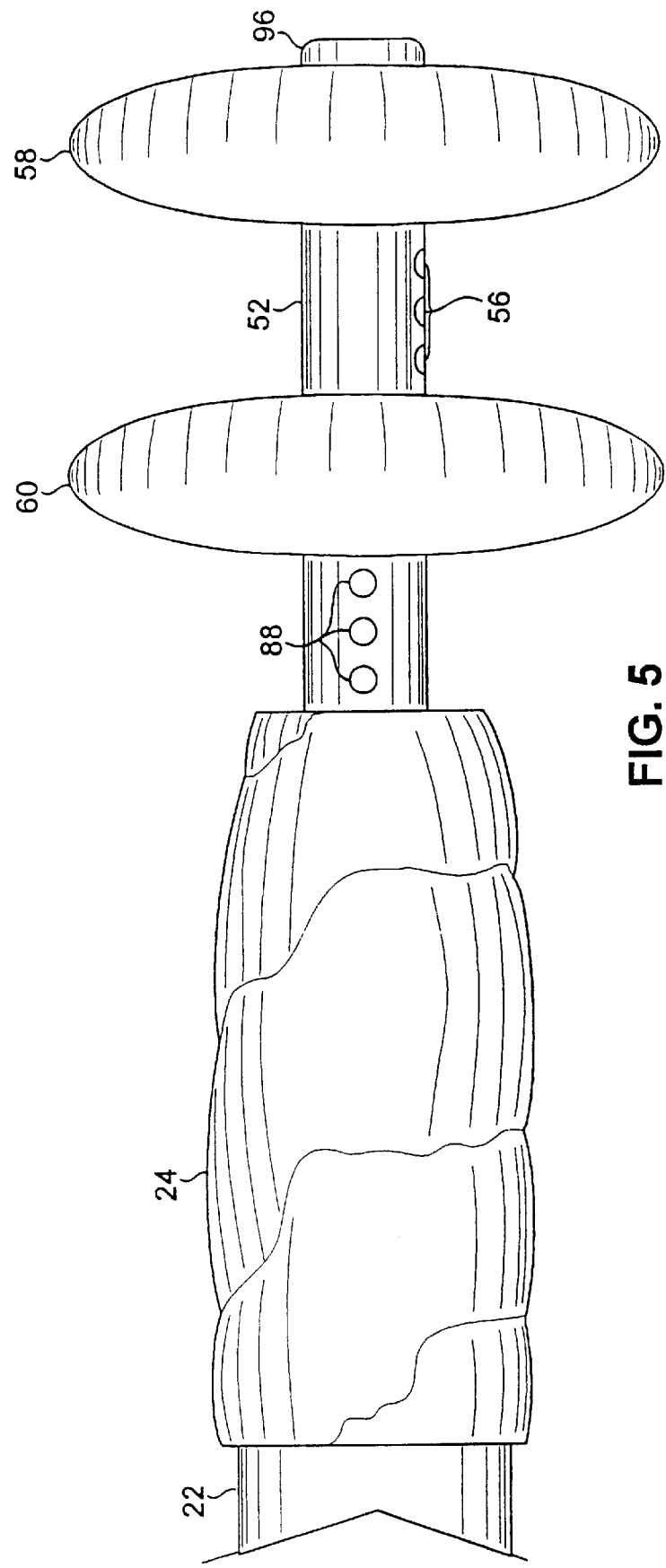
FIG. 5 is a side view of the distal portion of the catheter of FIG. 1, wherein two occlusion balloons are inflated.

In FIGS. 4 and 5, the dilation-drug delivery catheter 10 of the present invention is shown in its drug delivery position. In FIG. 4, the dilation portion 20 is shown retracted to fully reveal the distal end of the drug delivery portion 50 of the catheter 10, which comprises the occlusion balloons 58, 60, and the drug delivery ports 56. FIG. 5 is a side view of the catheter 10, showing the occlusion balloons 58, 60, inflated as they would be immediately prior to and during drug delivery. The present invention enables a plurality of drug delivery ports 56 to be provided between the occlusion balloons 58, 60, better ensuring the delivery of an adequate quantity of drug. Perfusion openings 88 are preferably provided through the walls of the inner catheter shaft 52 to the guide wire lumen 64 as shown in FIG. 5, to provide a path for blood to flow beyond the occluded site. There are preferably between 2–20 circular or oval perfusion openings 88 with a diameter or length, respectively, of between about 0.003–0.020 inches. Three perfusion openings 88 are provided in this embodiment.

Returning to FIG. 1, the proximal end of the catheter 10 includes a Y-adaptor 68 including a port 66, as is known in the art. A tube (not shown) is connected to the dilation lumen 38 of the outer catheter shaft 22 and extends through the port 66. The outer catheter shaft ends within the Y-adaptor 68, proximate the base of the port 66. A syringe can be used to supply the dilation fluid through the port 66 into the dilation lumen 38, also as is known in the art. A Tuohy-Borst adapter 70 is threaded on the central port of the Y-adaptor 68. The inner catheter shaft 52 extends through the Y-adaptor 68 and Tuohy-Borst adapter 70. In this embodiment, three tubes 72, 74, and 76 are connected to the drug delivery lumen 54, inflation lumen 62 and guide wire lumen 64, respectively, of the inner catheter shaft 52. Hubs 78 are connected to each tube. The guide wire can be inserted into the guide wire lumen 64, through tube 76. Syringes can also be used to supply inflation fluid for the occlusion balloons 58, 60 and any desired drug through tubes 74 and 72, respectively.

The outer diameter of the catheter 10 and the deflated dilation balloon 24 is preferably no greater than about 0.042–0.050 inches, so that it can be used with a 7 or 8 French guiding catheter. To accommodate the tubes 72, 74, 76, the portion of the inner catheter shaft 52 which extends out of the Tuohy-Borst adapter 68 flares to an outer diameter of about 0.200 inches at about point 80. The tubes 72, 74, 76, are held together by a heat shrink tubing 82.

The distal end 84 of the inner catheter shaft 52 preferably includes a resilient tip 96 which comprises a material softer than that of the inner catheter shaft 22. The tip 96 spreads or bends when it contacts body tissue, easing the catheter's passage through the vascular system and helping to avoid tissue damage. The tip 96 can be made of ultra low density polyethylene 4603 from Dow Chemical Corporation, which has a melt flow rate at 190° C. (ASTM D-1238) of 0.7–0.9 g/10 min. and a density (ASTM D-792) of 0.9030–0.9070 g/cc. The tip 96 can also be a nylon, such as PEBA 25D from Elf Atochem Deutschland GmbH, which has an ultimate tensile strength (ASTM D-638) of 4950 psi min., an ultimate elongation (ASTM-638) of 640% min., a flexural modulus (ASTM D-790) of 2100 psi min., a Durometer (ASTM D-2240) of 25D±4D, and a melting point (ASTM D-3418) of 142°–153° C. The tip 96 can be connected to the inner catheter shaft 22 by an adhesive or thermal bonding.

Radiopaque markers 86 of gold or tantalum, for example, are also preferably provided on the inner catheter shaft 52 within the occlusion balloons 58, 60, and on the outer catheter shaft 22 within the dilation balloon 24, as shown, to assist in monitoring the position of the catheter on a fluoroscope during a PTA or PTCA procedure, as is known in the art. The inner catheter shaft 52 and occlusion balloons 58, 60, are preferably coated with a lubricous material, such as silicone, acrylimide, or a hydrophilic polyurethane coating, to ease retraction of the dilation portion 20 after dilation. The outer catheter shaft 22 and dilation balloon 24 can be similarly coated to ease its advance through a guiding catheter and a lesion, as is known in the art.

The inner and outer catheter shafts can be of any material suitable for catheters, such as linear low density or high density polyethylene, nylon, polyurethane, polypropylene, silicone rubber, or other non-thrombogenic materials. A linear low density polyethylene which can be used for the outer catheter shaft 22 is Dowlex 2038 from Dow Chemical Company, which has a melt flow rate at 190° C. (ASTM D-1238) of 0.85–1.15 g/10 min. and a density (ASTM D-792) of 0.9330–0.9370 g/cc. A high density polyethylene which can be used for the outer catheter shaft 22 is LB 8320-00 from Quantum Chemical Corporation, which has a melt flow rate at 190° C. (ASTM D-1238) of 0.20–0.36 g/10 min. and a density (D-1505) of 0.9566 g/cc min.

A nylon which can be used for the inner or outer catheter shafts 22, 52 is nylon 12, such as L2101F Vestamed from H üls America Inc., which has a relative viscosity (ISO 307) of 2.05–2.22 and a water content (ASTM D-4019) of 0.10 maximum. Another nylon which can be used is PEBA 70D from Elf Atochem, which has an ultimate tensile strength (ASTM D-638) of 8300 psi min., an ultimate elongation (ASTM D-638) of 400% min., a flexural modulus (ASTM D-790) of 67,000 psi min., a Durometer (D-2240) of 69D±4D and a melting point (ASTM D-3418) of 160°–180° C.

A high density polyethylene which can be used for the inner catheter shaft 52 is LM6007 from Quantum Chemical Corporation, which has the following characteristics:

| | |
|---|---|
| Ultimate Tensile Strength (ASTM D-638) | 4400 psi min. |
| Ultimate Elongation % at break (ASTM D-638) | 600% min. |
| Durometer D Scale (ASTM D-2240) | 68 ± 4.5 |
| Melt Flow Rate at 240° C. 2160 g (ASTM D-1238) | 0.070 (REF) |
| Flexural Modulus at Room Temperature (ASTM D-790, Procedure B) | 220,000 psi min. |
| Vicat Softening Point °C. (ASTM D-1525) | 125° C. (REF) |

The outer catheter shaft 22 and inner catheter shaft 52 are extruded separately. To form the flared portion of the inner catheter shaft 52, a bump extrusion process can be used, as is known in the art. After extrusion of the inner catheter shaft 52, the tubes 72, 74 and 76 are inserted into the shaft's wider portion and thermally bonded in place. An adhesive can be used, as well. A tube (not shown) is inserted and similarly bonded to the dilation lumen 38 of the outer catheter shaft 22. That tube extends through the port 66 of the Tuohy-Borst adaptor 70.

After formation of the inner catheter shaft 52, the perfusion openings 88 and drug delivery ports 56 are made. Passages through the shaft 52 to the inflation lumen 62 proximate the intended location of the occlusion balloons, are also made. The radiopaque markers 86 are added to the inner and outer catheter shafts, as well. All these procedures are known in the art.

The dilation balloon 24 can be of any type and size appropriate for PTA and PTCA procedures. For example, the balloon 24 can be of polyethylene, polyethylene terephthalate, nylon, polyurethane, or any other material suitable for a dilation balloon. The balloon 24 can be compliant, non-compliant, or semi-compliant. The dilation balloon 24 can be attached to the outer catheter shaft 22 through thermal bonding, including laser bonding or ultrasonic bonding, or with an adhesive, as is known in the art. An apparatus and process for laser bonding angioplasty balloon catheters is disclosed in U.S. Pat. No. 5,267,959, which was filed on Nov. 29, 1991 by the inventor of the present invention and is assigned to the assignee of the present invention. U.S. Pat. No. 5,267,959 is incorporated by reference herein. The balloon 24 is preferably of the same or compatible material as the catheter shaft 28, to enable thermal bonding.

A low density polyethylene which can be used for the dilation balloon 24 is P.E. 1031 from Rexene Corporation, which has a melt flow rate at 190°±0.2° C. (ASTM D-1238) of 0.4–1.4 g/10 min., a density (ASTM D-1505) of 0.93±0.02 g/cc and a melt point (ASTM D-3417, D-3418) of 104°–140° C. A linear low density polyethylene which can be used is Dowlex 2247A LLPDE from Dow Chemical Corporation, which has a melt index at 190° C./2.16 kg (ASTM D-1238) of 2.0–2.6 g/10 min., a density (ASTM D-1505) of 0.9150–0.9190 g/cc, and a melt point (D-3417, D-3418 (REF)) of 122°–125° C.

The occlusion balloons 58, 60 can be nylon, polyamide copolymer, polyethylene, polyethylene terephthalate, polyurethane, Kraton, silicone, latex or any other soft, non-thrombogenic material which will seal against, but not expand, the arterial wall when inflated. The balloons can be tubes which expand on inflation or blow molded balloons. If the balloon material is compatible with the inner catheter shaft 52, the occlusion balloons 58, 60 can be attached by the thermal bonding techniques discussed above. If not, an adhesive may be used. A nylon which can be used for the occlusion balloons 58, 60 is L25 G Grilamid from EMS-Chemie AG, which has a melting point of 178° C., a density (DIN 53479) of 1.01 Kg/dm$^3$, a tensile strength (DIN 53455) of 40 N/mm$^2$, an elongation at yield (DIN 53455) of 10% and a Shore D hardness (DIN 53505) of 72.

The dilation-drug delivery catheter 10 of the present invention can be introduced into the vascular system and advanced to the site of the stenosis by a guiding catheter, as would an ordinary dilation catheter. After a guide wire is advanced through the stenosis, the catheter 10 is advanced from the guiding catheter, over the guide wire, through the stenosis.

Dilation fluid is injected with a syringe through the port 66 of the Y-adaptor 68, to the dilation lumen 38, to dilate the balloon 24 as shown in FIG. 2, opening the stenosis, as would an ordinary dilation catheter. After the stenosis is opened, the dilation balloon 24 is deflated and the dilation portion 20 of the catheter 10 is retracted far enough to reveal the drug delivery ports 56, the proximal occlusion balloon 60 and the perfusion openings 88, if present, putting the catheter into the drug delivery position of FIG. 4. The dilation portion can be retracted by loosening the Tuohy-Borst adaptor 70 and withdrawing the outer catheter 22 a suitable distance. After the dilation portion 20 is retracted, the Tuohy-Borst adapter is tightened.

If the perfusion openings 88 are present, the guide wire is also preferably retracted to a position proximal to the perfusion openings 88 to allow blood to flow through the inner catheter shaft 52. If active perfusion is required, the guide wire can be completely removed and blood or perfluorochemicals such as Fluosol® can be injected with a syringe through tube 76, as is known in the art.

Inflation fluid is then injected with a syringe through the tube 74 to inflate the distal and proximal occlusion balloons 58, 60, until the occlusion balloons meet and seal the arterial wall, isolating the dilated region. Antithrombolytic, antiproliferative, or any other type of drug, can now be injected through tube 72, drug delivery lumen 54 and drug delivery ports 56, via a syringe, to the dilation site.

After the drug has been applied at the desired pressure and for the desired length of time (typically from about 20 seconds to 3 minutes), the occlusion balloons are deflated and the dilation-drug delivery catheter 10 is withdrawn from the blood vessel. One drug formulation which may be promising is dexamethasone absorbed in poly-lactic/poly-glycolic particles with diameters substantially less than 100 microns. Such particles can adhere to or penetrate the arterial wall. The surface of the particles can be treated with cell adhesion proteins and peptides based peptides to improve the adhesion of the particles with the arterial wall. An arginine glycine aspartic acid based peptide which can be used is Teptite 2000® from Telios Pharmaceuticals, Inc.

The dilation-drug delivery catheter of the present invention provides a single catheter which can perform dual functions, saving time and enabling delivery of drug directly to the dilation site.

I claim:

1. A dilatation-drug delivery catheter comprising:
   (a) an outer catheter having a distal portion, the outer catheter comprising:
      (i) a dilatation balloon disposed at least partially about the outer catheter distal portion;
      (ii) an inflation lumen in communication with the dilatation balloon; and
      (iii) a central lumen sized and configured to receive an inner catheter; and
   (b) an inner catheter movably disposed at least partially within the outer catheter and having a distal portion, the inner catheter comprising:
      (i) at least one drug delivery port configured in the inner catheter distal portion;
      (ii) a drug delivery lumen in communication with the at least one drug delivery port; and
      (iii) a guidewire lumen sized and configured to receive a guidewire
   wherein the dilatation-drug delivery catheter further includes perfusion means comprising at least one passage through the inner catheter to the guidewire lumen.

2. The catheter of claim 1 wherein the outer catheter is adapted for proximal movement relative the inner catheter to expose the at least one drug delivery port.

3. The catheter of claim 1 comprising a plurality of drug delivery ports.

4. The catheter of claim 1 further comprising a lubricious layer between the inner and outer catheters.

* * * * *